US009808261B2

(12) United States Patent
Gelaude et al.

(10) Patent No.: US 9,808,261 B2
(45) Date of Patent: Nov. 7, 2017

(54) CUSTOMIZED SURGICAL GUIDES, METHODS FOR MANUFACTURING AND USES THEREOF

(75) Inventors: Frederik Gelaude, Leuven (BE); Tim Clijmans, Heverlee (BE)

(73) Assignee: Materialise N.V., Leuven (BE)

(*) Notice: Subject to any disclaimer, the term of this patent is extended or adjusted under 35 U.S.C. 154(b) by 398 days.

(21) Appl. No.: 13/515,141

(22) PCT Filed: Dec. 28, 2010

(86) PCT No.: PCT/EP2010/070777
§ 371 (c)(1),
(2), (4) Date: Jun. 11, 2012

(87) PCT Pub. No.: WO2011/080260
PCT Pub. Date: Jul. 7, 2011

(65) Prior Publication Data
US 2012/0289965 A1    Nov. 15, 2012

Related U.S. Application Data

(60) Provisional application No. 61/290,673, filed on Dec. 29, 2009.

(30) Foreign Application Priority Data

Dec. 29, 2009 (GB) .................................. 0922640.8

(51) Int. Cl.
| *A61B 17/56* | (2006.01) |
| *A61B 17/15* | (2006.01) |
| *A61B 17/17* | (2006.01) |
| *B33Y 80/00* | (2015.01) |

(Continued)

(52) U.S. Cl.
CPC .............. *A61B 17/15* (2013.01); *A61B 17/17* (2013.01); *A61B 17/1746* (2013.01); *A61B 2017/568* (2013.01); *A61B 2034/108* (2016.02); *A61F 2/34* (2013.01); *B33Y 80/00* (2014.12); *Y10T 29/49764* (2015.01)

(58) Field of Classification Search
CPC ................ A61B 17/17; A61B 17/1746; A61B 2017/320052; A61B 2019/508
USPC ........................................ 606/87-89, 91, 99
See application file for complete search history.

(56) References Cited

U.S. PATENT DOCUMENTS 4,019,827 A *  4/1977  Christianson et al. ....... 408/202
4,715,860 A   12/1987  Amstutz et al.
4,721,104 A    1/1988  Kaufman et al.
(Continued)

FOREIGN PATENT DOCUMENTS

WO    2005037114 A1    4/2005
WO    2009121144 A1   10/2009

OTHER PUBLICATIONS

The International Search Report dated Mar. 14, 2001 for PCT Application No. PCT/EP2010/070777.
(Continued)

*Primary Examiner* — Anu Ramana
(74) *Attorney, Agent, or Firm* — Amster, Rothstein & Ebenstein LLP

(57) ABSTRACT

The invention relates to surgical guides which are of use during reconstructive bone surgery for guiding a surgical instrument or tool. More particularly, the guides are characterized in that they are fitted to the implant rather than to the bone.

15 Claims, 10 Drawing Sheets

(51) Int. Cl.
  *A61F 2/34* (2006.01)
  *A61B 34/10* (2016.01)

(56) References Cited

U.S. PATENT DOCUMENTS

| | | |
|---|---|---|
| 5,141,680 A | 8/1992 | Almquist et al. |
| 5,192,539 A | 3/1993 | Van Der Marel et al. |
| 5,976,149 A * | 11/1999 | Masini ............... A61B 17/1746 606/91 |
| 7,153,309 B2 | 12/2006 | Huebner et al. |
| 8,133,234 B2 * | 3/2012 | Meridew et al. ............... 606/91 |
| 2005/0085818 A1 | 4/2005 | Huebner |
| 2005/0148843 A1 | 7/2005 | Roose |
| 2005/0234461 A1 | 10/2005 | Burdulis, Jr. et al. |
| 2006/0173458 A1 | 8/2006 | Forstein et al. |
| 2007/0233112 A1 | 10/2007 | Orbay et al. |
| 2008/0183172 A1 | 7/2008 | Fritzinger |
| 2009/0088865 A1 | 4/2009 | Brehm |
| 2009/0163922 A1 | 6/2009 | Meridew et al. |
| 2009/0312760 A1 | 12/2009 | Forstein et al. |
| 2010/0082035 A1 | 4/2010 | Keefer |
| 2011/0093086 A1 | 4/2011 | Witt et al. |
| 2011/0106086 A1 | 5/2011 | Laird |
| 2011/0301655 A1 | 12/2011 | Price et al. |
| 2014/0135940 A1 | 5/2014 | Goldstein et al. |

OTHER PUBLICATIONS

The International Preliminary Report on Patentability dated Apr. 24, 2012 for PCT Application No. PCT/EP2010/070777.
Communication European Search Report dated Mar. 2, 2015 from the European Patent Office in connection with European Patent Application No. 14193082.6, 6 pages.

* cited by examiner

CUSTOMIZED SURGICAL GUIDES, METHODS FOR MANUFACTURING AND USES THEREOF

CROSS-REFERENCE TO RELATED APPLICATIONS

This application is a U.S. National phase of PCT Application No. PCT/EP2010/070777, filed Dec. 28, 2010, which claims priority to U.S. Provisional Application No. 61/290,673, filed Dec. 29, 2009 and European Application No. 0922640.8, filed Dec. 29, 2009.

FIELD OF THE INVENTION

The present invention relates to surgical guides which are of use during reconstructive bone surgery, more specifically during reconstructive joint surgery, for guiding a surgical instrument or tool. The present invention further relates to methods for manufacturing these surgical guides and specific methods for using the surgical guides of the invention in reconstructive bone and joint surgery.

BACKGROUND

In most bone or joint arthroplasty, replacement and/or reconstruction surgery procedures, a bone or a joint is replaced by a prosthetic implant. The main goal of an arthroplasty intervention is to relieve (arthritis) pain or to restore severe physical joint damage resulting from, for example, trauma. When a prosthesis fails, a revision arthroplasty is carried out. This procedure is technically more difficult and time-consuming than the primary intervention and the outcome is often less satisfactory, both because there is less bone stock to work with and because the removal of adherent cement or prosthetic components may result in fracture or perforation of the bone. With each successive joint revision, the risk of infection and symptomatic loosening of the prosthesis may increase substantially. Revision surgeries become more frequent as the population grows older and patients receive prostheses at an earlier age.

The treatment of bone and joint defects has gradually become more complex. While it started out with standard interventions using off-the-shelf prosthesis components, it has evolved to patient-specific surgery plans and patient-specific implant designs. The accurate and stable fixation of implants onto the bone or joint, while increasingly difficult, remains one of the most important steps in arthroplasty interventions.

The standard process of fixing or anchoring an implant with screws into the bone is mostly a two-step procedure. First, the screw trajectory is pre-drilled with a dedicated instrument. This is followed by the screw insertion along the pre-drilled screw trajectory. Some self-tapping screw types do not require pre-drilling; direct insertion of the screw, directly establishes the screw trajectory.

Unfortunately, this anchoring process has a number of important drawbacks.

Indeed, deviations in direction and/or location of the screw trajectory often lead to a suboptimal screw traction which may cause soft tissue damage. The pre-drilling and/or placing of the screws are often done by the surgeon freehand style, with only a limited view on the bone through the available surgical incision. Moreover, where the surgeon has sufficient exposure of the patient and a wide view on the implant and screw hole and is able to orient the pre-drilling instrument in any orientation (which is not often the case), he will typically use the surface curvature of the implant around the screw hole as a visual reference and will aim at placing the instrument orthogonally with respect to the local implant surface. As a result, the obtained screw directions are often suboptimal and/or deviate from a preoperative plan. Screws can for example be directed in bone of low quality, or have only limited traction length. In addition, a shift of the implant away from the optimal location before pre-drilling has started can cause screw locations, i.e. insertion points of the screw trajectories into the bone, to deviate from a predetermined location.

Deviations in the direction and/or location of a screw trajectory may also cause the screws to become mutually intersecting, causing e.g. the insertion of a first screw (either with or without a planned direction) to block the insertion of the next. Unused screw holes badly influence the implant's long-term integrity, unless some other portion of the implant compensates the local decrease in material volume. This however implies the use of more implant material, for example thickening of the implant, making it more bulky, and/or requires larger contact regions with the bone. The latter again is detrimental to soft tissue preservation.

Specific tools and technologies have been developed in the past in order to solve the above problems associated with the fixation or anchoring process of the implant.

Navigation technology has for instance been used as a global positioning system for the surgeon. For example, infrared sensors placed near the bone or joint in the operating room act like satellites constantly monitoring the location of markers and instruments placed along a patient's anatomy. Unfortunately, this technology is expensive and intra-operatively very time-consuming.

A system for fixation of an implant onto a bone is provided in U.S. Pat. No. 7,153,309 (Huebner et al.), in which a guide device is attached to a bone plate. The use of this device is in practice however limited to anatomical areas which can be extensively exposed or can be easily approached from different directions. For example, the device does not allow pre-drilling from the ipsilateral side of a bone plate, a procedure which is however often needed, for example in implant surgery of the hemi-pelvis, scapula, or mandible. US2008/0183172 describes a guide for a bone plate which is more compact but similarly comprises a projection extending from the guide which is configured to be received within an aperture in the bone plate for securing the plate guide to the plate. The aperture can be a bone-screw receiving aperture inherently present on existing bone plates or an aperture designed to receive a projection comprising a resilient finger. These devices can however only be applied in cases of bone repair (following traumata, with multiple bone fragments), and not for bone and joint repair such as in arthroplasty. In addition, the described plate-guide fixation systems define the direction and insertion point of a connective feature with respect to the plate, and (only if the plate is patient-specific) also with respect to the bone. Accordingly, absolute referencing, needed to transfer a preoperative surgery plan on the patient bone geometry and derived from medical images onto the patient's bone during surgery, is not guaranteed. Finally, the guides are physically attached to the plate, requiring attachment features on both components and moreover requiring assembly manipulations.

Standard-size drill guiding cylinders have been described, which can be screwed into the implant screw hole (such as for example for the Compliant Pre-Stress (CPS) device of Biomet Inc.; Warsaw, Ind.). Due to reasons of manufacturability, machine set-up time and costs, this guiding solution is limited to large series of off-the-shelf implants, for which it is economically profitable to set up expensive threading machinery.

Patient-specific bone guides have a unique (partial) fit with a portion of the surrounding bone, and therefore allow the guiding of features, such as bone drilling and/or cutting elements, in an unambiguous and accurately planned trajectory or direction into the bone (Tardieu P B (2007) Int. J. Periodontics Restorative Dent. 27(2): 141-149; Kunz M (2007) Proceedings of the 7*th* Annual Meeting of CAOS-International: 159-161; Lombardi Jr A V et al. (2008) BFA Orthopedics; 31: 927). However, a custom bone guide is not always a guarantee for adequate implant fixation, especially in the case of a patient-specific implant. For certain anatomical regions, and especially in complex revision cases, the only bone regions which can be exposed and reached through the surgical window are few, small and spread out. One could think of a patient-specific implant reaching out to these regions for fixation. Pre-drilling screw holes could be performed with a plastic implant replica serving as a base frame for the bone guides. This is however unpractical and ineffective since the guide-frame construction has to be taken out, and the implant reinserted while keeping track of the pre-drill locations. Furthermore, the use of a Kirchner wire to keep track of the pre-drill locations while sliding off the guide and sliding the implant on is not convenient and not fully constrained.

Accordingly, there is a need for alternative and improved (customized) surgical guides, which are stable and which provide the ability to accurately insert a surgical instrument into a patient's bone or joint.

SUMMARY OF THE INVENTION

The present invention relates to customized surgical guides for patient-specific bone implants, which ensure a stable guidance of the surgical instrument into the bone as well as an accurate fixation of the bone implant. Instead of being mounted onto one or more patient-specific surfaces of the bone, as in surgical bone guides, the guides according to the present invention are directly positioned onto the final patient-specific bone implant. This is ensured by a specific fit between the customized surgical guide and one or more surface structures of the patient-specific bone implant and/or by the patient-specific localization and orientation of the guiding elements. Upon using the customized surgical guides according to the invention, the patient-specific implant can be directly placed in its final and correct position onto the bone avoiding the risk of inaccurate re-insertion after pre-drilling or other preparatory operations, which is often a problem when using customized bone guides. Accordingly, the customized guides according to the present invention allow for a much more correct and accurate fixation of the implant onto the bone in comparison with the known surgical guides used in bone and/or (complex) joint arthroplasty.

In a first aspect, the present invention provides customized surgical guides for patient-specific bone implants, more particularly bone implants having a patient-specific morphology, most particularly bone prostheses. The customized surgical guides for surgical instruments for placement on a patient-specific implant according to the invention comprise (i) one or more customized surface structures extending over at least part of the patient-specific morphology of the implant, and/or (ii) one or more customized guiding elements, and are characterized in that the guide and the bone implant engage by means of a unique fit, ensured by the complementarity between said patient-specific morphology of said bone implant and at least one of said one or more customized surface structures.

In particular embodiments, the customized surgical guides according to the present invention are specifically suitable for placement on a bone implant having a patient-specific morphology, i.e. a shape which is specific for each patient and comprise (i) one or more customized surface structures extending over at least part of the patient-specific morphology of the implant, and (ii) one or more customized guiding elements and are characterized in that the customized surgical guide and the patient-specific bone implant engage by means of a unique fit, ensured by the complementarity or congruency between said patient-specific morphology and at least one of said one or more customized surface structures. In the latter embodiments, the unique fit is optionally further ensured, by the position and orientation of the customized guiding elements.

In particular embodiments, the one or more customized surface structures of the surgical guides of the invention extend along the patient-specific surface of the implant in at least two, more particularly at least three different main directions, to further ensure the stability of the guides.

In particular embodiments, the customized surgical guides for patient-specific bone implants, and more particularly the customized surface structures thereof are made by additive manufacturing.

In particular embodiments, the customized surgical guides of the invention may further comprise one or more connecting structures, interconnecting the one or more surface structures and the one or more guiding elements. In these specific embodiments, the one or more guiding elements may be attached to the one or more connecting structures.

In further particular embodiments, the one or more surface structures and/or the one or more guiding elements and/or the connecting structure of the customized surgical guides of the invention may comprise one or more locking features, which can be integrated in the surface structures or connecting structure and/or which may be extensions of the one or more guiding elements. These one or more locking features serve to lock the surgical guide to the patient-specific implant in a certain fixed position. In particular embodiments, the surgical guides according to the invention do not comprise a dedicated locking feature.

In certain embodiments, the one or more guiding elements of the customized surgical guides of the invention are drill guiding elements or cutting guiding elements. In further particular embodiments, the guiding elements further comprise a stop, such as a drill stop or a cutting stop.

In particular embodiments, the customized surgical guides according to the present invention further comprise an element, such as for example a wing element, serving as a visual reference.

In particular embodiments, the customized surgical guides are designed to fit on a patient-specific acetabular implant. In a further particular embodiment of such guides for a patient-specific acetabular implant, the connecting structure is a ring structure, fitting on the acetabular rim of an acetabular implant and the at least one or more surface structures are designed to fit on one or more surfaces of the patient-specific acetabular implant. More particularly, the customized surgical guide and the acetabular implant engage in a unique fit ensured by the congruency, more particularly the complementarity between the patient-specific (external) morphology of the acetabular implant and at least one of said one or more customized surface structures and/or the orientation and position of the guiding elements. In particular embodiments the unique fit ensured by the congruency or complementarity between the patient-specific (external) morphology of the acetabular implant and at least one of the one or more customized surface structures, fitting on the surface of the patient-specific acetabular implant. Such surfaces of the patient-specific acetabular implant optionally include surfaces which are designed for positioning on the ischium, ilium and/or the pubis and optionally ensure replacement of one or more parts thereof. Indeed, in particular embodiments the implant is designed based on information obtained from patient-specific medical images of the ischium, ilium and/or the pubis and uniquely matches with the specific bone geometry of the ischium, ilium and/or the pubis of the patient in which it is introduced resulting in a patient-specific morphology of the implant. In a particular embodiment, one surface is provided which is designed for positioning on the ilium.

In yet a further aspect, the present invention provides methods for manufacturing customized surgical guides for a patient-specific bone implant according to the invention. In particular embodiments, the methods of the present invention comprise a manufacturing process which ensures that the guiding elements are positioned corresponding to pre-determined screw insertions, and one or more surface structures of the guide fit specifically on the patient-specific bone implant.

In particular embodiments, the methods comprise the steps of: (a) obtaining an image of the bone and the design of the patient-specific implant thereon; (b) determining one or more screw trajectories using a planning; (c) designing a customized surgical guide such that the guiding elements are positioned corresponding to the pre-determined screw trajectories, and one or more surface structures provide a supportive structure connecting the one or more guiding elements and fit specifically on the patient-specific bone implant; and (d) manufacturing the customized surgical guide based on the information provided in step (c).

In further particular embodiments, the methods for manufacturing a customized surgical guide for surgical instruments for placement on a patient-specific bone implant according to the invention, comprise the steps of: (a) designing a customized surgical guide comprising one or more custom guiding elements and one or more customized surface structures based on: (i) an image of the bone and the patient-specific bone implant thereon and (ii) the one or more screw trajectories determined by pre-operative planning; The methods further comprise step (b) of producing, by an additive manufacturing technique, the customized surgical guide based on the design obtained in step (a), wherein: the one or more guiding elements of said guide are positioned corresponding to the pre-operatively planned screw trajectories, and the one or more customized surface structures of the guide ensure a unique fit between the patient-specific bone implant and the guide by way of the congruency, more particularly the complementarity between the customized surface structure and the patient-specific morphology of the patient-specific bone implant.

In particular embodiments of the methods of the present invention it is envisaged that the one or more guiding elements of the guides are positioned to correspond to one or more screw trajectories which have been determined through pre-operative planning. According to particular embodiments, the methods comprise the step of determining one or more screw insertions using a planning taking into account one or more of the following criteria:

obtaining an optimal number of non-intersecting drill directions for screw trajectories ensuring that the screw trajectories run through bone volume with the optimal available quality ensuring optimal screw trajectory length and ensuring that the surrounding healthy soft tissue is optimally preserved.

In particular embodiments the step of ensuring that the screw trajectories run through bone volume with the optimal available quality is determined from grey values in medical images.

The customized surgical guides obtainable by the methods according to the present invention not only ensure an improved accuracy compared to prior art guiding tools, but in addition make it possible to provide guidance in complex bone reconstructions. Thus, surgical guides obtainable by the methods of the present invention are novel and inventive over the standard guides or even the alleged "custom" guides disclosed in the prior art.

In a further aspect, the present invention provides combinations of a patient-specific bone implants, and a customized surgical guide according to the invention. It will be understood that the customized surgical guides according to the invention are designed to fit specifically onto the patient-specific bone implant of the combination.

In a further aspect, the present invention relates to the use of the guides according to the invention for fixing a patient-specific bone implant onto a bone. More particularly, the invention provides methods for fixing a patient-specific bone implant onto a bone, comprising the steps of: (a) placing a customized surgical guide according to the invention onto a patient-specific bone implant; (b) introducing the screw trajectories with the appropriate surgical tools; (c) removing the customized surgical guide; and (d) fixing the patient-specific bone implant with screws onto the bone, whereby step (d) of fixing the patient-specific implant can be either prior to or after step (c), or both.

The invention further provides computer programs for performing the methods of the present invention, more particularly, computer program products for enabling a computer to execute all or part of the methods according to the invention described herein. More particularly, computer programs are provided for providing a design of a customized surgical guide comprising one or more custom guiding elements and one or more customized surface structures based on (1) one or more images of the bone and the patient-specific bone implant thereon; and (2) one or more screw trajectories determined by pre-operative planning, wherein the one or more guiding elements of the guide are positioned corresponding to the pre-operatively planned screw trajectories, and the one or more customized surface structures of the guide ensure a unique fit between the patient-specific bone implant and the guide by way of a congruency or complementarity between the customized surface structure(s) and the patient-specific morphology of the patient-specific bone implant.

BRIEF DESCRIPTION OF THE DRAWINGS

The following description of the figures of specific embodiments of the invention is merely exemplary in nature and is not intended to limit the present teachings, their application or uses. Throughout the drawings, corresponding reference numerals indicate like or corresponding parts and features.

Figure 1:
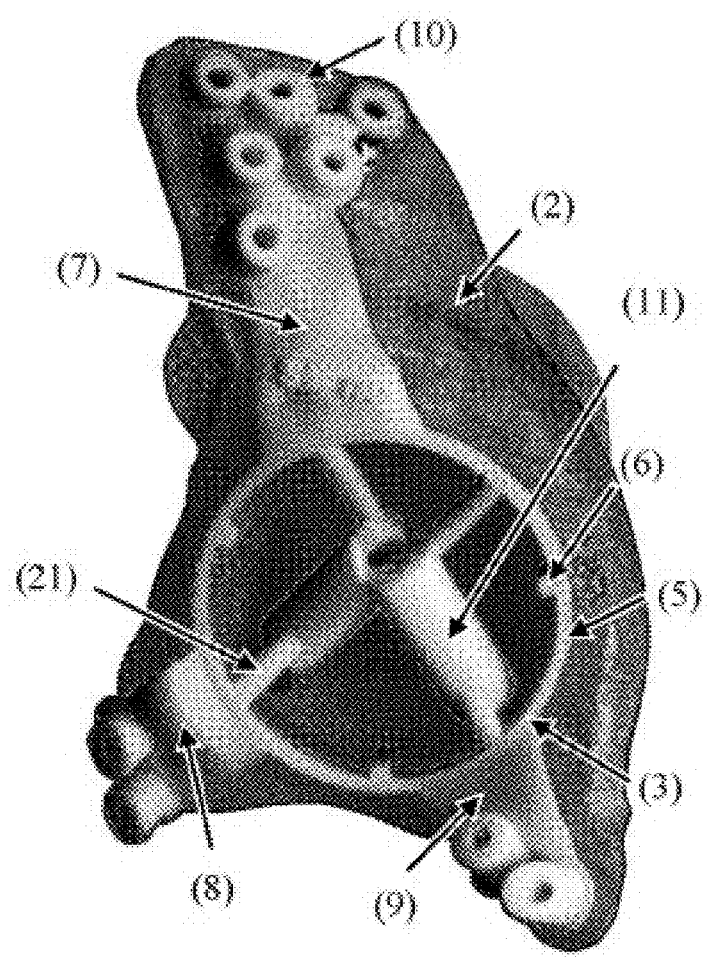
FIG. 1 Example picture of a customized surgical drill guide for a patient-specific acetabular implant according to a particular embodiment of the present invention.

List of reference numerals used in the Figures. Each of these illustrations represent particular embodiments of the features concerned and the corresponding features are not to be interpreted as limited to this specific embodiment.
(1) Bone model: left hemi-pelvis
(2) Patient-specific acetabular implant
(3) Customized surgical guide according to a specific embodiment of the invention
(4) Drill directions or screw trajectories
(5) Central (interconnecting) ring structure, designed to fit specifically with the acetabular rim of the patient-specific implant according to a specific embodiment of the invention
(6) Locking features (an example, e.g. on central ring Structure (5))
(7), (8) and (9) One or more surface structures
(10) and (11) One or more guiding elements
(12) Implant screw holes
(13) Acetabular rim of the patient-specific implant
(14) Cavity formed by the acetabular portion of the patient-specific implant
(15) Ends of cylindrical guiding elements, which are trimmed either straight, obliquely or with a complexly shaped cut
(16) Extension of cylindrical guiding elements
(17), (18) and (19) Patient-specific areas on external surface of an acetabular implant
(20) Disc-shaped visual reference ring
(21) Bridging element
(22) Wing element serving as a visual reference for performing a surgical interaction
(23) Cylindrical guiding elements that are halved lengthwise

DETAILED DESCRIPTION

The present invention will be described with respect to particular embodiments but the invention is not limited thereto but only by the claims. Any reference signs in the claims shall not be construed as limiting the scope.

Where the term "comprising" is used in the present description and claims, it does not exclude other elements or steps. Where an indefinite or definite article is used when referring to a singular noun e.g. "a" or "an", "the", this includes a plural of that noun unless something else is specifically stated.

Furthermore, the terms first, second, third and the like in the description and in the claims, are used for distinguishing between similar elements and not necessarily for describing a sequential or chronological order, unless specified. It is to be understood that the terms so used are interchangeable under appropriate circumstances and that the embodiments of the invention described herein are capable of operation in other sequences than described or illustrated herein.

The terms or definitions used herein are provided solely to aid in the understanding of the invention.

The present invention provides customized surgical guides for patient-specific bone (or joint) implants, which allow both a stable introduction of a surgical instrument into a bone (or a joint) as well as ensuring an accurate fixation of the implant onto the bone (or joint).

The term patient-specific implant as used herein refers to an implant of which at least part is shaped to match the specific bone geometry of a patient. Thus, a guide according to the present invention is envisioned to fit specifically onto an implant which itself is specific for a particular patient. In the context of the present invention, and more particularly when referring to the unique fit of the guide on the patient-specific implant, the terms "congruency" and "complementarity" are used. It is considered that two surfaces are "congruent", when the surface features match, which can be as a result of a similarity of features (one surface corresponding essentially to a mold taken from the other) and/or as a result of the fact that one or more specific features of one surface are designed to fit onto the other surface. The term "complementary" more strongly emphasizes the similarity of the features. In the context of a patient-specific implant this typically implies that the one or more contact surface(s) of the implant are complementary to the remaining area(s) of the bone or joint, and thereby ensure a (patient)-specific fit. This specific fit of the implant is ensured during the planning and design of the implant, and may imply that in specific areas a clearance of between 0.1 and 0.5 mm between the implant CAD model and the prepared bone CAD model is envisaged. In the context of the guides of the present invention, this implies that the one or more contact surface(s) and/or guiding elements of the guide are complementary to the external surface of the implant, such that they ensure a (patient- and implant-) specific fit.

In particular embodiments of the present invention, the patient-specific implants are replacement bone prostheses, i.e. they replace at least part of a bone or joint lost by injury (traumatic) or missing from birth (congenital). This type of replacement bone prosthesis is different from medical devices such as screws or plates which merely serve to secure existing bone parts to each other. These patient-specific implants, in addition to comprising a surface which is complementary to the remaining area(s) of the bone or joint on which the implant is to be fitted, moreover mimic and/or functionally replace the surface of the original (i.e. non-injured) and absent piece of the bone or joint. Preferably, where possible, the surface of these implants seamlessly connect to the remaining surfaces of bone adjoining the implant site. Thus, in particular embodiments, the patient-specific implants according to the present invention are characterized by an "external" morphology which is patient-specific. The "external" morphology comprises one or more surfaces of the implant which replaces the original surface of the bone or joint. In these embodiments the implant is not only designed to fit specifically onto remaining areas of the bone or joint to ensure a seamless restoration of the injured bone or joint, but additionally, in view of the fact that the implant at least partially replaces one or more anatomical features of the bone or joint, mimics and/or functionally replaces the original anatomical features of the bone or joint.

Patient-specific implants have the advantage that they have a better anatomic fit compared to conventional standard implants. This reduces operating time and results in a longer-lasting and better functioning implant. Moreover, in specific cases of reconstructive bone and joint surgery, for example cases with large bone defects and/or malformations, patient-specific implants are simply the only alternative as off-the-shelf implants are just unable to provide stable support and fixation, and functioning. Patient-specific implants are typically designed based on medical images (such as a Computed Tomography (CT) data set) of the bone. A patient-specific implant may include an off-the-shelf implant which is adjusted (e.g. pre-bent) to the shape of the bone (and/or bone defect) of the patient prior to the start of surgery. Patient-specific implants preferably have not only a single fit (i.e. only one position fits), but also a unique fit with the bone structure in which they are introduced (i.e. fitting only on the specific patient). In addition, optimally, as detailed above, patient-specific implants may have a patient-specific external morphology. This unique fit corresponds to the position of the surgical guide on the implant envisioned in the planning of the surgical intervention.

More particularly, in particular embodiments the present invention provides customized surgical guides for surgical instruments suitable for placement on patient-specific bone implants, which are positioned onto the patient-specific bone implant (and not or not exclusively onto the bone), by specifically fitting onto one or more surfaces of the patient-specific implant. At the same time, the customized surgical guides according to the invention establish absolute directions and/or locations of drill and/or cut trajectories since the patient-specific implant fits specifically onto the bone, and the guide fits uniquely (i.e. only in that position) onto the patient-specific implant.

The customized surgical guides of the present invention comprise at least one or more surface structures and one or more guiding elements. In particular embodiments, at least one of the one or more surface structures is designed to fit specifically onto the external morphology of the patient-specific bone implant. The different components of the surgical guides according to the present invention are described more in detail hereafter.

The customized surgical guides according to the present invention comprise one or more surface structures which are structures which extend over at least part of the patient-specific surface of the implant. The one or more surface structures may have one or both of the following functions. In particular embodiments, the one or more surface structures ensure the unique fit of the surgical guides with the patient-specific implant. Accordingly, the surface structures comprise one or more areas by which the correct placement of the guide on a patient-specific implant is ensured. In particular embodiments, such surface structures coincide with and follow (i.e. are congruent or complementary to) the outer structure (or external morphology) of the implant.

The one or more surface structures of the customized surgical guides according to the present invention may also serve as a base or supportive structure for the one or more guiding elements of the guides.

In particular embodiments, the outer structure or external morphology (i.e. the structure on the side of the implant which does not contact the bone in which the implant is fit) of the patient-specific implant is patient-specific. The customized guide is designed to fit uniquely (i.e. only in one position) onto the outer structure of the patient-specific implant.

In particular embodiments, one or more of the surface structures of the customized surgical guides of the invention comprises, on the side designed to fit onto the surface of the implant, at least an area (hereinafter also referred to as an 'implant-specific area') which is exactly and fully complementary, i.e. specifically fits onto a specific area of the patient-specific bone implant, on which the guide is to be placed.

In particular embodiments, the congruency or complementarity between the area on the patient-specific implant and the area on at least one of the surface structures of a customized guide according to the invention may involve a clearance between the guide surface and the bone implant. In particular embodiments, this specific fit involves planning a clearance of between 0.1-0.5 mm in the implant-specific area(s) between the guide and the implant.

In these specific embodiments of the invention, (i.e. wherein one or more of the surface structures comprises an implant-specific area) when one or more implant-specific areas of the one or more surface structures are contacted with or positioned opposite to their corresponding complementary surfaces of the patient-specific bone implant, the surfaces fit, mate and/or engage, thereby fixing the guide into a predetermined position. This position is not only the single position in which the surgical guide can be placed on the implant, but is also "unique" to the patient-specific implant (i.e. the guide will not fit with the same accuracy on another implant). Accordingly, in these embodiments, a unique fit between the guide and the implant is ensured by the one or more surface structures, more particularly by the implant-specific areas thereon.

It is noted that the customized guides according to these embodiments of the invention, while intended to fit uniquely onto a patient-specific implant, may, in addition to the surfaces or parts thereof which ensure the unique fit with the patient-specific implant, comprise surfaces or parts thereof which, upon placement, contact the bone and are supported by the bone. Optionally, the one or more surfaces or parts thereof contacting the bone, may comprise areas which specifically mate with areas of the bone.

In specific embodiments, the three-dimensional fit of the contact area between the one or more surface structures of the custom surgical guide and the patient-specific implant ensures the stability of guide positioned onto the implant by preventing both translation and rotation (either uni- or bi-directionally) along and/or around a certain axis.

Alternatively, where the outer surface of the patient-specific bone implant is generic, such an area of a surface structure may be customized to fit a specific area of this generic outer surface. Moreover, the outer surface of the patient-specific implant may comprise both patient-specific and more generic parts, such that the one or more surfaces of the customized guides of the invention may comprise one or more areas with a generic fit and one or more areas with a patient-specific fit.

The exact size and shape of the one or more surface structures of the guide are not critical to the invention but will be determined by the shape of the patient-specific implant. In particular embodiments the patient-specific areas on the one or more surface structures encompass at least 30% of the surface of the guide which contacts the implant. More particularly, this extends to at least 50%, even more particularly to between 50 and 90, or even to more than 95% of the surface of the guide contacting the implant. As detailed above, the patient-specific areas may also comprise sections which contact the bone.

In particular embodiments, the surface structures correspond to flanges, i.e. longitudinal structures which extend in one or more different directions and allow for exact and stable fitting of the custom guide onto the implant and/or supporting of one or more guiding elements for making drilling or cutting trajectories from the implant into one or more underlying bone structures. According to these embodiments, customized surgical guides with one or more, two or more, three or more flanges are envisaged. Such flanges may be connected through one or more connecting structures as detailed below. In particular embodiments, the one or more customized surface structures of the surgical guides of the invention extend along the patient-specific surface of the implant in at least two, more particularly at least three different directions, to further ensure the stability of the guides. In further particular embodiments the customized guides according to the present invention comprise at least three flanges which, projected onto a plane extend into three directions on the surface (in the plane of the surface) of the implant of which at least two directions are separated less than 180° C.

In particular embodiments, the one or more surface structures of the customized surgical guides of the invention, irrespective of their other features, may comprise one or more locking features, which provide an (additional) interlock of the surgical guide with the patient-specific guide. Such interlocking features may be a three-dimensional feature designed specifically on a guide/implant combination. The unique fit of the guide with the implant is ensured by the surface structures and/or guiding elements alone, but locking features may further ensure maintenance of the guide in the unique fit position. In particular embodiments, the guides according to the invention do not comprise a specific locking feature. In further particular embodiments, the surgical guides according to the invention do not comprise a locking feature on a surface structure.

The customized surgical guides of the present invention further comprise one or more guiding elements for guiding a surgical instrument or tool into the bone (or joint) of a patient. The one or more guiding elements each contain at least one means of guiding an instrument such as but not limited to a drill, bur, saw, jig saw, lateral drill or any other cutting, milling or drilling instrument or any other tool such as a fastener, more particularly a screw, the orientation and position of which corresponds to a planning.

Where the tool is a screw or the surgical instrument is a drill or bur, a guiding element of the surgical guide according to the invention may comprise at least a cylindrical hole. Where the guide is a drill guide, the diameter of the drill guiding element is determined based on the diameter of the pre-drill instrument. In particular embodiments, where the surgical instrument is a saw, jig saw, mill or lateral drill, a guiding element may contain at least a (narrow) slot or flat surface. The height of the one or more guiding elements of the surgical guide according to the invention is determined to provide sufficient stability and/or guidance to the surgical instrument which is to be introduced.

The guiding element of the surgical guide according to the invention are typically cylindrical, but the ends (15) may be trimmed either straight, obliquely or with a complexly shaped cut (see FIG. 2E), in order to fit the available working space and/or surgical window. More specifically, the entire customized surgical guide has to fit into the typically V-shaped surgical incision space during application, and should therefore enable (temporary) soft tissue overlay when put under—for instance—muscles.

The one or more guiding elements can optionally include a safety stop to prevent a surgical instrument from advancing beyond a planned depth into the bone. For example, in the case where the surgical instrument to be introduced into the bone or joint is a drilling instrument, such as a drill or a bur, drill stops may be used to prevent the surgical drill from advancing beyond a planned or determined depth into the bone. Alternatively, in the case where the surgical instrument to be introduced into the bone or joint is a cutting instrument, such as a saw or a jig saw, cutting stops may be used to prevent the surgical cutting instrument from advancing beyond a planned or determined depth into the bone.

Figure 6:
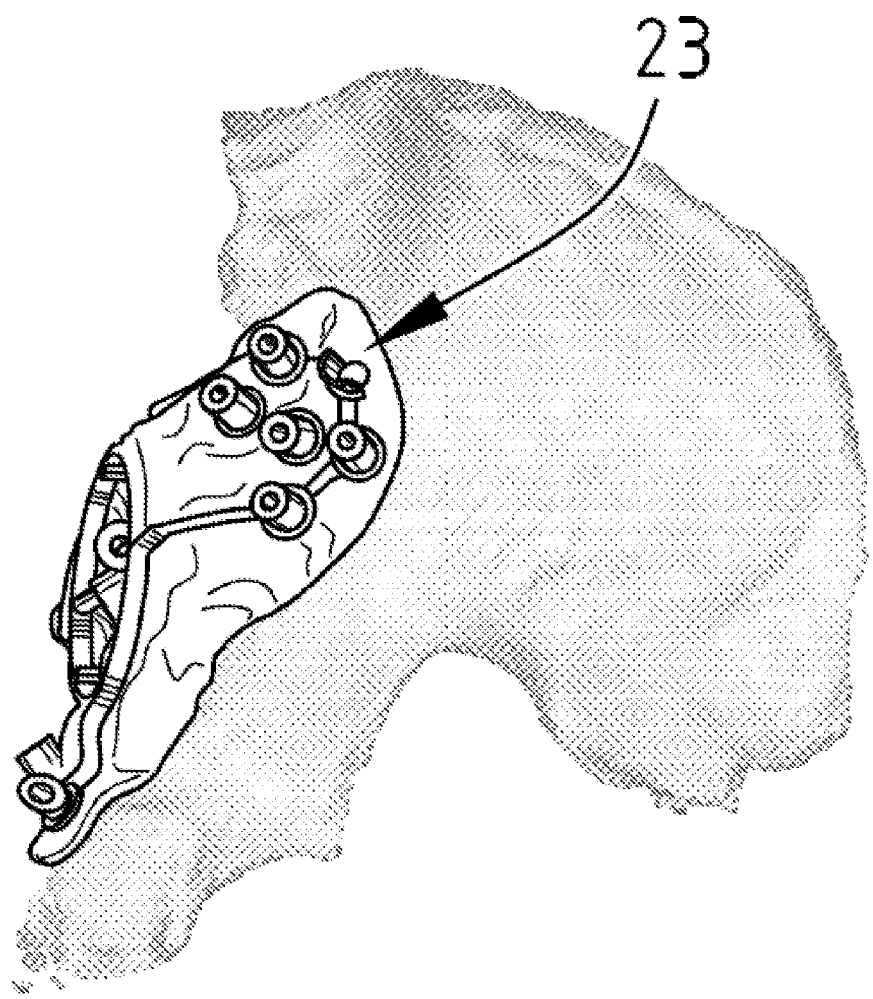
FIG. 6 A customized surgical guide according to a particular embodiment of the invention comprising a cylindrical drill guiding element that is halved lengthwise, allowing for instance (partial) insertion of a screw directly in the implant, and subsequent removal of the customized guide with the inserted screw left in place.

The guiding elements can further be adjusted to allow fastening of the implant prior to drilling and/or removal of the guide. For instance, a cylindrical drill guiding element can be halved lengthwise (as shown in FIG. 6), allowing (partial) insertion of a screw directly in the implant, and subsequent removal of the customized guide with the inserted screw left in place. Doing so reduces degrees of freedom of the patient-specific implant and customized guide during drilling, and assures that correspondence between pre-drills and screw holes is not lost. For instance, where the type of screw is a self-tapping type of screw, pre-drilling is not required, allowing direct insertion of the screw and immediate establishing of the screw trajectory along the predetermined path.

The position of a guiding element comprised in the surgical guides according to the present invention is typically determined by the planned direction of a surgical instrument into the bone or joint. As such the guiding elements are "customized" to the specific requirements as determined by the planning. The patient-specific implant will typically be provided with holes corresponding to the pre-determined screw insertions and the position of the guiding elements in the corresponding custom surgical guide is ensured to allow guiding of a surgical instrument through these holes.

In particular embodiments, the customized guiding elements ensure (optionally in addition to implant-specific surface structures described above) a unique fit of the surgical guide with a patient-specific implant. Indeed, it is envisaged that a unique fit between the implant and the guide can be ensured by matching of the guiding elements on the implant according to the pre-determined operative planning. Accordingly, in particular embodiments, the unique fit is ensured by the guiding elements or a combination of guiding elements and implant-specific surface structures. In particular embodiments, the unique fit between the implant and the guide is ensured by at least 30% of the total contact surface (i.e. including implant-specific surfaces and guiding elements) between the guide and the implant, more particularly by at least 50% of the total contact surface, even more particularly by at least 75% of the total contact surface. In particular embodiments the unique fit is ensured by 95 to 100% of the total contact surface of the guiding element.

As determined by the nature of the implant, the guiding elements are positioned on the one or more surface structures and/or on the connecting structure. Elements of the connecting structure which ensure the connection of one or more guiding elements with the remainder of the surgical guide are also referred to herein as 'bridging elements'.

The one or more guiding elements are positioned either on the one or more surface structures or on the one or more connecting structures (as further described herein) such that a surgical instrument which is passed through the one or more guiding elements can engage the bone or joint at a desired location. The position of the one or more guiding elements is also such that it allows insertion of a surgical instrument. In specific embodiments, the directions of the one or more guiding elements are mutually intersecting in order to allow the guiding elements to all be positioned within the available working space and/or surgical window.

In particular embodiments, the one or more guiding elements of the customized surgical guides of the invention may comprise one or more locking features, which help to ensure a specific and stable fit with the patient-specific implant. In particular embodiments, this locking feature comprises an extension of the guiding element which fits into the implant screw hole, while still allowing insertion of the surgical instrument, as for example shown in FIG. 4. In further particular embodiments, the guides of the present invention do not comprise a specific (i.e. independent) locking feature. In further particular embodiments, the surgical guides of the invention do not comprise a dedicated locking feature on a guiding element.

As mentioned above, according to specific embodiments, the surgical guides of the present invention may further comprise one or more connecting structures, which directly or indirectly connect the one or more surface structures to the one or more guiding elements in the customized surgical guides according to the invention.

The one or more connecting structures of the surgical guides according to the present invention must be sufficiently rigid, so as to ensure the desired stability and accuracy upon use of the guide, and should nevertheless be as open as possible, so as to allow visual verification for the surgeon of the good fit of the surgical guide. Accordingly, in particular embodiments, the one or more connecting structures of the surgical guides according to the present invention ensure a mechanically rigid but (from a utilitarian point of view) versatile connection between the one or more surface structures and the one or more guiding elements in the customized surgical guides, such that the position of the different components of the guide relative to each other is fixed.

Similar to the surface structures described above, the one or more connecting structures comprised in the customized surgical guide according to the invention may have one or more of the following functions. In addition to serving to interconnect the one or more surface structures and the one or more guiding elements, the one or more connecting structures may serve as a base or supportive structure for one or more guiding elements. Additionally or alternatively, the one or more connecting structures may help to ensure a specific fit with the patient-specific implant.

As will be detailed below, where the customized surgical guide according to the invention is a customized guide for a patient-specific acetabular implant, the one or more connecting structures can comprise a ring structure designed to fit specifically with the acetabular rim of the patient-specific implant. The one or more connecting structures further comprise bridging structures, which ensure the connection of one or more guiding elements for guiding surgical tools into the acetabular cup with the remainder of the surgical guide.

In further particular embodiments, the one or more connecting structures of the customized surgical guides of the invention comprise one or more locking features, which ensure an additional interlock with the patient-specific implant. Where the one or more connecting structures comprise a circular ring designed to fit on an acetabular rim of an acetabular implant, such locking features can be positioned on the ring structure to ensure an interlock with the acetabular rim of the patient-specific implant. As detailed above, however, in particular embodiments, the surgical guides of the present invention do not comprise a locking feature, more particularly do not comprise a locking feature on the connecting structure.

Figure 2A:
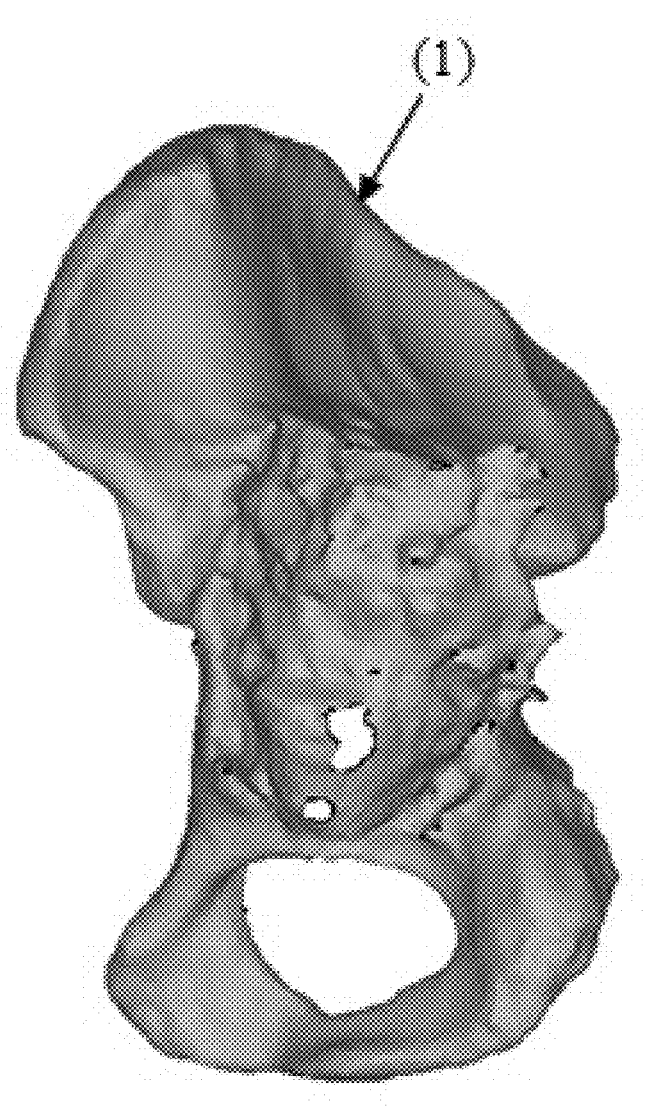
FIG. 2A Drawing of a left hemi-pelvis with a large acetabular bone defect
Figure 2B:
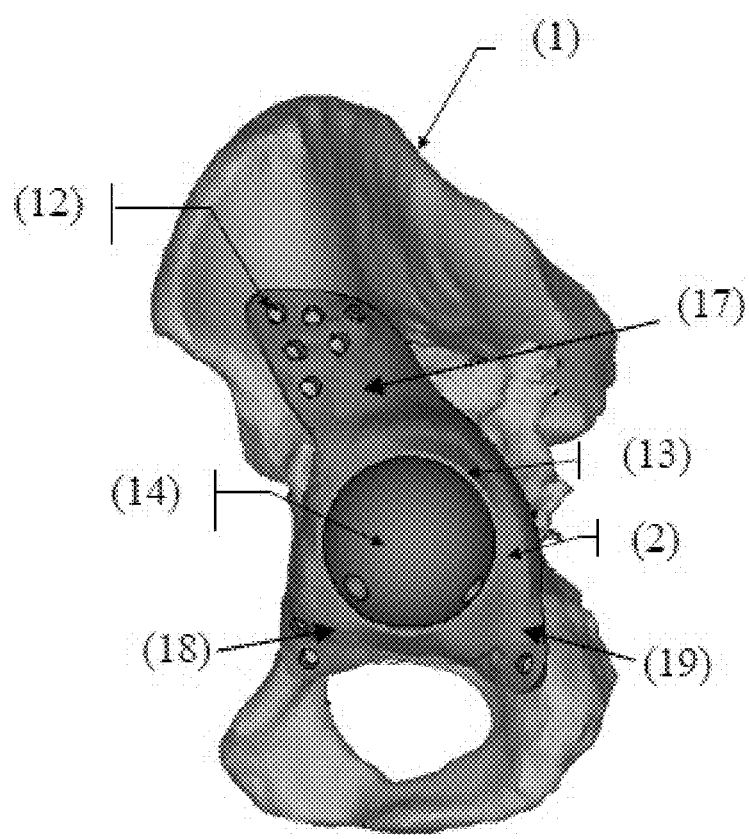
FIG. 2B Drawing of a left hemi-pelvis with a large acetabular bone defect reconstructed by a patient-specific acetabular implant.
Figure 2C:
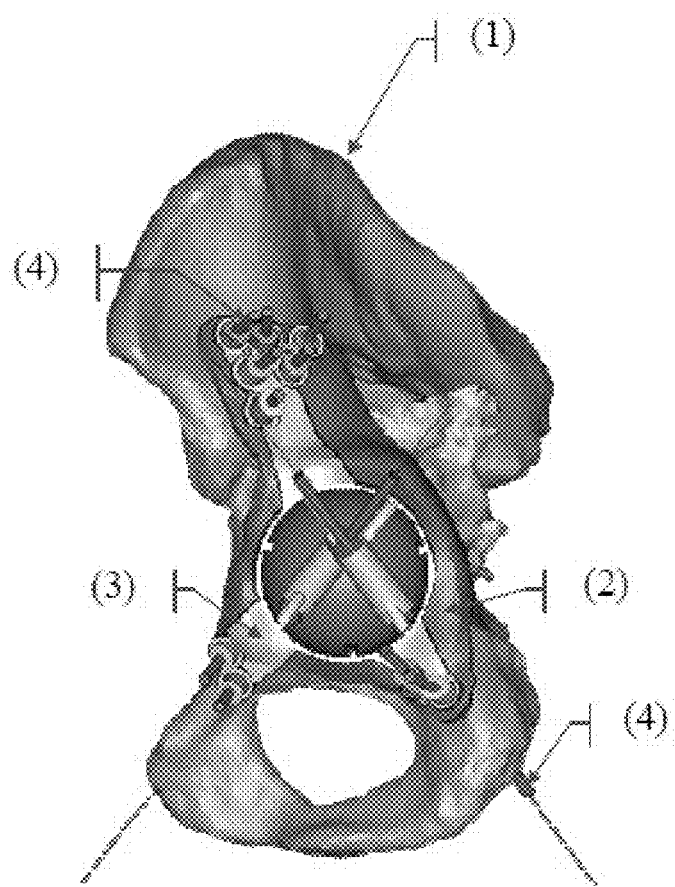
FIG. 2C Complete assembly of a left hemi-pelvis with a large acetabular bone defect with a patient-specific implant and a customized surgical guide according to a particular embodiment of the invention.
Figure 2D:
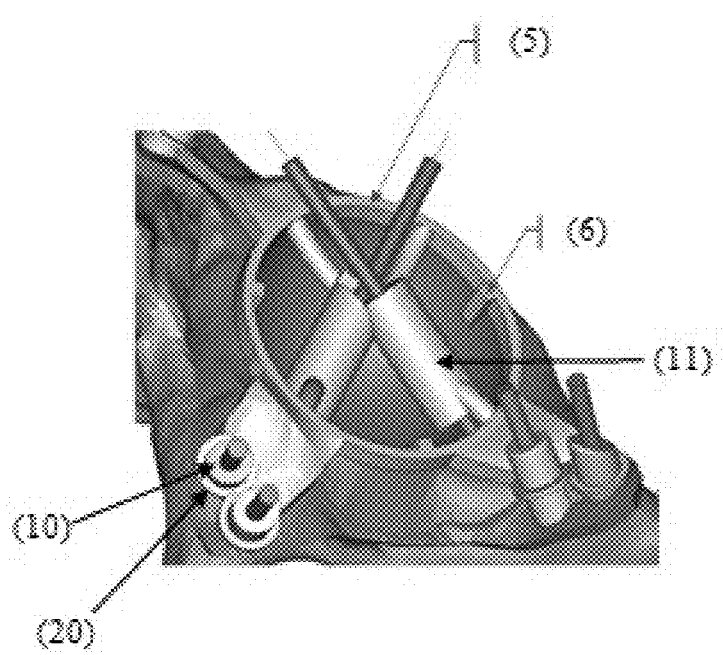
FIG. 2D Zoomed view on the central portion of a customized surgical guide according to a particular embodiment of the invention.
Figure 2E:
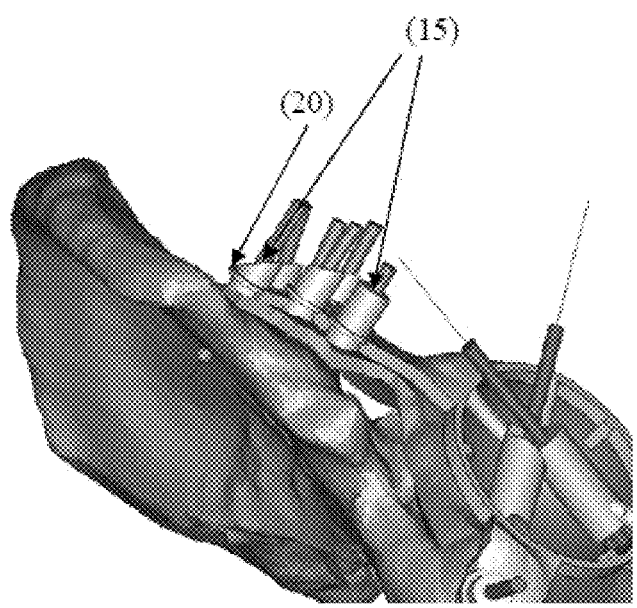
FIG. 2E Zoomed view on cylindrical drill guiding elements of a customized surgical guide according to a particular embodiment of the invention, wherein the guiding elements are positioned on the patient-specific ilium area of the implant.
Figure 4:
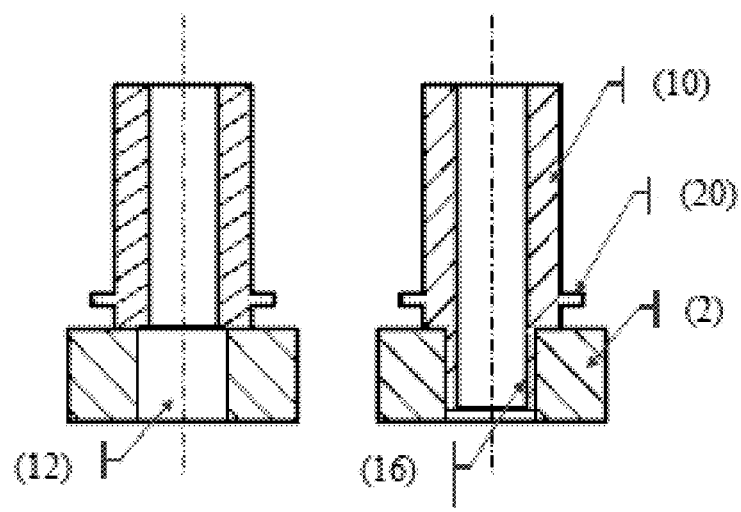
FIG. 4 Cross-sectional view of a cylindrical drill guiding element of a customized surgical guide according to a particular embodiment of the invention, with (right) and without (left) extension.
Figure 5:
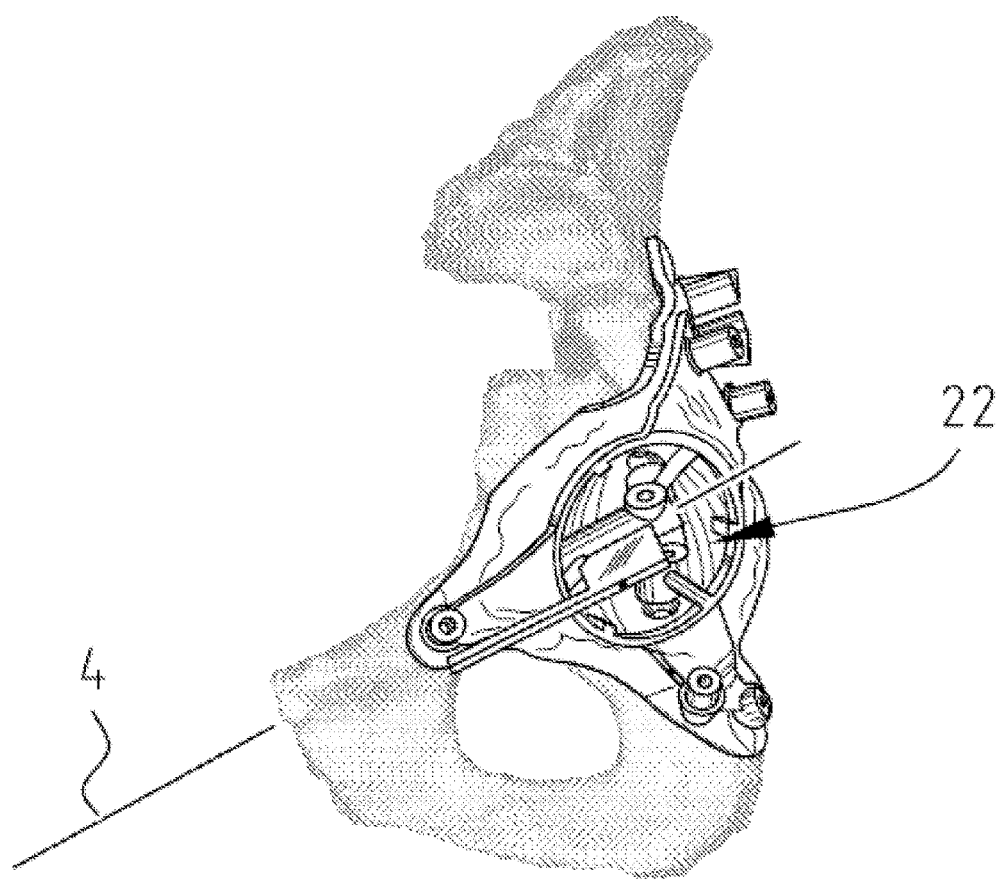
FIG. 5 A customized surgical guide according to a particular embodiment of the invention comprising a wing element serving as a visual reference for performing a surgical interaction.

The customized surgical guiding tools of the present invention may further comprise one or more features for visual referencing, to solve orientation problems in case of complexly shaped guiding elements. These visual references may optionally be attached to the surgical guides to provide a (visual) feedback to the surgeon, more particularly in case of drill guiding elements with overlying soft tissue, minimizing potential misinterpretation resulting from obscured anatomical reference points, or potentially confusing orientations of the surface structures of the customized guide. Such visual reference may for example include a reference disc (20), as shown in FIGS. 2E and 4, whereby the plane formed by the disc is perpendicular to the planned drill direction. Additionally or alternatively, the customized guide according to the present invention may further comprise one or more elements, such as wing elements (22), exemplified in FIG. 5, or planar discs, indicating the direction and/or position of the one or more drill guiding elements of the guide and thus also serving as a visual reference. Such visual references can be attached to a drill guiding element or any other portion of the customized guide.

In a further aspect, the present invention provides combinations of a patient-specific bone implant and a customized surgical guide according to the invention (as described above). Indeed, it is the object of the present invention to provide a customized surgical guide which fits specifically onto a patient-specific bone implant. Accordingly, as the surgical guide is designed to fit specifically on the bone implant, it is envisaged that the implant and guide are provided in combination. In specific embodiments of combinations of a patient-specific bone implant and a customized surgical guide according to the invention (i.e. wherein one or more of the surface structures comprises an implant-specific area) when one or more implant-specific areas of the one or more surface structures are contacted with or positioned opposite to their corresponding complementary surfaces of the patient-specific bone implant, the surfaces fit, mate and/or engage, thereby fixing the guide into a predetermined position. This position is unique to the patient-specific implant, and since the patient-specific implant in turn has a unique position to the bone, the customized guide has a unique position to the bone.

The customized surgical guides according to the invention are envisaged for use with different types of bone implants. The surgical guides of the present invention are of particular interest for use in the fixation of bone implants in the context of complex bone reconstructions, i.e. where bone loss is observed. Thus, the guides of the present invention are particularly suited for implants which replace deficient or missing bone structures. The surgical guides of the present invention are also of particular use where a limited surgical window is/can be used. However, the customized surgical guides according to the present invention can be designed for any patient-specific implant. The use of patient-specific implants has a number of advantages compared to traditional off-the shelf implants. They ensure a better and tighter anatomic fit which results in a better stability and/or function (less aseptic loosening) and reduced damage to neighboring tissue. The time required by the surgeon for placement (operating time) is reduced. Moreover, for particular applications (such as in Cranio-Maxillo-Facial surgery) patient-specific implants ensure a more satisfying aesthetic result for the patient. Patient-specific implants are commonly used in orthopedic surgery of the knee, hip and shoulder, but the customized surgical guides according to the invention are equally suitable for use in combination with patient-specific implants for other joints or bones. Accordingly, the combinations according to the present invention are not limited by a specific type of patient-specific implant.

In particular embodiments, the combination of a customized surgical guide and a patient-specific implant according to the invention is a combination of a patient-specific acetabular implant and a customized surgical guide therefore. As detailed above, the customized surgical guide for an acetabular implant typically comprises one or more connecting structures comprising a ring structure and the at least one or more surface structures of the guide are designed to fit on one or more surfaces of the patient-specific acetabular implant. Typically a patient-specific acetabular implant comprises one or more extensions designed for positioning on one or more of the ischium, ilium and/or the pubis. In particular embodiments, the corresponding customized surgical guide comprises one or more surface areas which are designed to fit onto the one or more extensions of the implant. In a further particular embodiment the customized surgical guide comprises one surface structure designed to fit onto an extension of a patient-specific implant which fits onto the ilium.

The combinations according to the invention comprise, in addition to a patient-specific implant, a customized surgical guide therefore according to the invention. Accordingly, the customized surgical guide comprises at least one or more surface structures, and one or more guiding elements. Optionally, and as described in detail above, the customized surgical guide for use in a combination with the corresponding patient-specific implant comprises one or more connecting structures interconnecting the one or more surface structures and the one or more guiding elements.

In particular embodiments of the combinations comprising a patient-specific bone implant and a customized surgical guide according to the invention, the one or more surface structures and/or the one or more guiding elements and/or the connecting structure of the customized surgical guides may comprise one or more locking features, which can be integrated in the surface structures or connecting structure and/or which may be extensions of the one or more guiding elements and which ensure (additional) specific interlock with the patient-specific implant. In particular embodiments, the surgical guides of the present invention do not comprise a dedicated locking feature, more particularly do not comprise extensions such as those described above.

In further particular embodiments of the combinations according to the invention, the one or more guiding elements of the customized surgical guides are drill guiding elements (or even cutting guiding elements). In further particular embodiments, the guiding elements further comprise a stop, such as a drill stop.

Particular embodiments of the combinations of the present invention comprise a patient-specific implant and two or more customized surgical guides.

As detailed above, the customized surgical guides and the combinations thereof with patient-specific implants according to the present invention are suitable for use in any type of bone or joint surgery procedure, such as for example bone or joint replacement surgery and/or bone or joint reconstruction surgery. Some non-limiting examples of joints in which patient-specific implants may be used and thus in which the customized surgical guides and the combinations thereof with patient-specific implants according to the present invention can be applied include the hip joint (or acetabulofemoral joint) between the femur and acetabulum of the pelvis, the shoulder joints (such as the glenohumeral joint between the humerus and the lateral scapula), the wrist joint (or radiocarpal joint) between the radius and the carpus, the elbow joints (such as the humeroulnar joint between the ulna and the humerus), the knee joints (the femoropatellar articulation between the patella and the femur or the femorotibial articulations between the femur and the tibia), and the ankle joint (or talocrural joint) between the tibia and fibula. Non-limiting examples of bone surgery procedures in which the customized surgical guides and the combinations thereof with patient-specific implants according to the present invention can be applied include intercalar resections, plating (osteosynthesis), epiphysis of long bones, diaphysis of long bones, treatment of comminuted fractures, and arthrodesis.

Accordingly, the customized surgical guides and the combinations thereof with patient-specific implants according to the present invention can be used in any type of bone or joint surgery procedure for the treatment of a variety of bone and/or joint diseases, including but not limited to osteoarthritis, rheumatoid arthritis, avascular necrosis, osteonecrosis, congenital disease, dislocation of a joint, joint dysplasia, frozen shoulder, loose shoulder, traumatized and maligned joint, and joint stiffness. In particular embodiments, the surgical guides and combinations thereof with patient-specific implants are used in the treatment of acetabular bone deficiencies. More particularly, the guides are of interest for use in acetabular defects which are optimally treated with patient-specific implants, such as those classified as type 3 or 4 deficiencies according to the AAOS classification (D'Antionio et al. 1999, Clin Orthop Rel Res, 243:126-137)) or as type IIIb according to the Paprosky classification (Paprosky et al. 1994, J Arthroplasty 9(1):33-44).

In a further aspect, the present invention provides methods for manufacturing customized surgical guides for patient-specific bone implants.

In particular embodiments, the methods for manufacturing a customized surgical guide for surgical instruments for placement on a patient-specific bone implant according to the invention comprise the steps of generating, a customized surgical guide wherein the one or more guiding elements of the guide are positioned corresponding to the pre-operatively planned screw trajectories and/or the one or more customized surface structures of the guide ensure a unique fit between the patient-specific bone implant and said guide by way of the congruency and/or complementarity between said customized surface structure and the patient-specific morphology of said patient-specific bone implant.

In further particular embodiments, this the guide is made by an additive manufacturing technique based on a design generated based on pre-operative planning. Thus in particular embodiments, the methods of the invention comprise:
(a) designing a customized surgical guide comprising one or more custom guiding elements and one or more customized surface structures based on:
   an image of the bone and the patient-specific bone implant thereon;
   the one or more screw insertions determined by pre-operative planning
(b) producing, by an additive manufacturing technique said customized surgical guide based on the design obtained in step (a), wherein:
   the one or more guiding elements of said guide are positioned corresponding to the pre-operatively planned screw trajectories, and
   the one or more customized surface structures of said guide ensure a unique fit between the patient-specific bone implant and said guide by way of the congruency between said customized surface structure and the patient-specific morphology of said patient-specific bone implant.

In further particular embodiments, the methods for manufacturing customized surgical guides according to the invention comprise the steps of:
(a) obtaining an image of the bone and the patient-specific implant thereon;
(b) determining one or more screw insertions using a planning;
(c) designing a customized surgical guide such that
   the guiding elements are positioned corresponding to the pre-determined screw trajectories, and
   one or more surface structures provide a supportive structure connecting the one or more guiding elements and fit uniquely on the patient-specific bone implant.
(d) producing said customized surgical guide based on the information provided in step (c).

Accordingly, the methods of manufacturing of the customized surgical guides according to the invention comprise the step of obtaining an image of the bone and the patient-specific implant thereon. Digital patient-specific image information can be provided by any suitable means known in the art, such as for example a computer tomography (CT) scanner, a magnetic resonance imaging (MRI) scanner, an ultrasound scanner, or a combination of Roentgenograms. A summary of medical imaging has been described in "Fundamentals of Medical imaging", by P. Suetens, Cambridge University Press, 2002.

For example, the step of obtaining an image of the bone and the patient-specific implant thereon may for example comprise the steps of (a1)) obtaining 2D datasets of the bone and (a2) reconstructing a 3D virtual bone model from said 2D datasets. Indeed, the first step in a planning is the construction of a 3D virtual model of the bone. This reconstruction starts with sending a patient to a radiologist for scanning, e.g. for a scan that generates medical volumetric data, such as a CT, MRI scan or the like. The output of the scan can be a stack of two-dimensional (2D) slices forming a 3D data set. The output of the scan can be digitally imported into a computer program and may be converted using algorithms known in the field of image processing technology to produce a 3D computer model of a relevant bone. Preferably, a virtual 3D model is constructed from the dataset using a computer program such as Mimics™ as supplied by Materialise N.V., Leuven, Belgium. Computer algorithm parameters are based on accuracy studies, as for instance described by Gelaude at al. (2008; Accuracy assessment of CT-based outer surface femur meshes Comput. Aided Surg. 13(4): 188-199). A more detailed description for making a perfected model is disclosed in U.S. Pat. No. 5,768,134 entitled 'Method for making a perfected medical model on the basis of digital image information of a part of the body'.

Once the 3D volume of the bone is reconstructed, the surgeon (or person skilled in the art) can define the position of the implant and the preferred position, orientation, depth and diameter of the screw trajectories using a planning which can be used to fix the implant to the bone. In non-limiting embodiments of the methods for manufacturing customized surgical guides according to the invention, the locations and/or directions of the one or more screw insertions are determined using a planning procedure, which is performed pre-operatively. Alternatively, a planning procedure in the methods for manufacturing the guides may be performed during the operation/surgery, without having performed a pre-operative planning step. The planning of the surgical intervention is done using suitable dedicated software, based on suitable medical images (of which CT, MRI, are examples), taking into account factors like bone quality and proximity to nerve bundles/blood vessels or other anatomically sensitive objects. To plan and simulate the intervention, images are imported into a computer workstation running 3D software. These images are manipulated as 3D surface meshes. The result is a computer simulation of the intervention, which outputs a planning containing the information necessary for adapting the orientation of the guiding elements.

In specific embodiments of the methods for manufacturing the customized surgical guides according to the present invention, the step of determining one or more screw trajectories comprises taking into account one or more of the following criteria:
   obtaining an optimal number of non-intersecting drill directions for screw trajectories;
   ensuring that the screw trajectories run through bone volume with the optimal available quality;
   ensuring optimal screw trajectory length; and
   ensuring that the surrounding healthy soft tissue is optimally preserved.

Accordingly, the step of determining one or more screw trajectories may comprise obtaining an optimal number of non-intersecting drill directions for screw trajectories. In order to obtain an optimal (which may imply a maximal) number of non-intersecting screw trajectories, a planning is performed by analyzing the bone and the patient-specific implant geometry. As a result, all of the screws for which screw holes were foreseen in the planning, can be placed during surgery. The number of screws is limited to the number actually useful. Foreseeing more screw holes than necessary would weaken the implant in view of long-term fatigue, and would enlarge the size of the implant. The latter would imply unnecessary sacrificing of healthy neighbouring soft tissues.

The step of determining one or more screw trajectories may further comprise ensuring that the screw trajectories run through bone volume with the optimal (which may imply the best) available quality. Thereto, planning is performed by analyzing the bone and patient-specific implant geometry, and the grey values retrieved from the medical images. As a result, screws are surrounded with bone with optimal traction strength.

In addition, the step of determining one or more screw trajectories may further comprise ensuring that an optimal (which may imply a maximal) screw trajectory length is established. Thereto, planning is performed by analyzing the bone and patient-specific implant geometry, and presence of implant components from foregoing surgeries which remain in place. As a result, screws have a practical and sufficient length in order to be useful and effective.

Finally, the step of determining one or more screw trajectories may further comprise ensuring that the surrounding healthy soft tissue is optimally (which may imply maximally) preserved. Thereto, a planning is performed by analyzing the soft tissue.

The process of locating screws directly relates to determining the extent of the surface of the patient-specific implant covering the bone through which the screws will be inserted. In view of postoperative restoration of patient functionality, screws protruding in—or implant portions overlaying—(healthy) soft tissues should be avoided as much as possible, as in the case of muscle attachments, or is simply impossible, as in the case of nerves and blood vessels.

The foregoing criteria for adequately determining one or more screw trajectories can be applied separately or, alternatively, can be combined. For example, the criterion of ensuring that the screw trajectories run through bone volume with the optimal available quality and the criterion of ensuring that an optimal (which may imply a maximal) screw trajectory length is established may be combined, resulting in the finding that screw trajectories which run through bone volume with good bone quality but which are only small in length (i.e. small bone depth), are useless. For instance, in normal patients the center of the iliac wing consists of a double layer of strong cortical bone, though the trajectory length that can be established measures less than about 2 mm and therefore renders this location impractical for positioning screws.

Also, the criterion of ensuring that the screw trajectories run through bone volume with the optimal (which may imply the best) available quality can be combined with the criterion of ensuring that an optimal (which may imply a maximal) screw trajectory length is established as well as with the criterion of ensuring that the surrounding healthy soft tissue is optimally preserved. For example, in determining the surface of the patient-specific acetabular implant covering the ilium, overlap with the gluteus medius muscle is preferably avoided.

In addition, during the planning of determining one or more screw trajectories the criterion of obtaining an optimal number of non-intersecting drill directions for screw trajectories may be combined with the criterion of ensuring that the screw trajectories run through bone volume with the optimal available quality as well as with the criterion of ensuring that an optimal (which may imply a maximal) screw trajectory length is established and with the criterion of ensuring that the surrounding healthy soft tissue is optimally preserved.

Having defined the preferred position, orientation, depth and diameter of the screw trajectories, this information can be used to design the customized surgical guide that fits perfectly when placed on the implant.

Designing a customized surgical guide according to the invention such that it fits on a patient-specific bone implant, comprises ensuring that the guiding elements are positioned corresponding to the pre-determined screw insertions, and that one or more surface structures provide a supportive structure connecting the one or more guiding elements and fit uniquely (and, where appropriate, specifically) on the patient-specific bone implant.

A preferred method for designing the surgical template uses a computer program such as 3-Matic™ as supplied by Materialise N.V., Leuven, Belgium. Alternatively, the surgical guide is automatically generated based on the information of preferred position, orientation, depth and diameter of the screw trajectories. In a particular non-limiting embodiment, this method uses a number of design parameters as an input including, but not limited to, the dimensions of the surgical tools as used by the medical practitioner, the contact area of the surgical guide with the patient-specific implant at the positions where the surgical tool is to be placed, etc.

More particularly the step of producing the customized surgical guide according to the invention implies producing and assembling the different parts thereof, i.e. producing one or more surface structures (as described herein), one or more guiding elements (as described herein), and optionally one or more connecting structures (as described herein), which interconnect the different parts of the guiding tool.

More particularly, the step of producing the customized surgical guide according to the invention implies positioning the one or more surface structures (as described herein), the one or more guiding elements (as described herein), and optionally the one or more connecting structures (as described herein) such that the guide fits perfectly and uniquely (i.e. only in that position) onto the patient-specific implant. The one or more surface structures of the customized surgical guides according to the present invention are positioned such that they may serve as a base or supportive structure for the one or more guiding elements of the guides and additionally or alternatively, that they may ensure the unique (and optionally, specific) fit of the surgical guides with the patient-specific implant. Indeed, where the outer surface (i.e. the surface opposite of the surface facing the bone) of the patient-specific implant corresponds to a standard shape (or one of a selection of standard shapes), the one or more surfaces are designed to ensure or to be able to ensure a "single fit" (i.e. only one position fits) with all implants having the same standard outer surface. Where the outer surface or external morphology of the patient-specific implant is also specific to the implant, these specific features may ensure a unique fit (i.e. only one position fits and only there is an optimal fit only on the corresponding implant and patient on which it is based) of the customized guide on to the patient-specific implant.

The position of the one or more guiding elements comprised in the surgical guides is determined by the planned direction of a surgical instrument into the bone or joint. As determined by the nature of the implant, the guiding elements are positioned on the one or more surface structures and/or on the one or more connecting structures. The position of the one or more connecting structures of the customized surgical guides according to the invention is preferably such that it provides, in addition to a connection between the one or more surface structures and the one or more guiding elements, a base or supportive structure for one or more guiding elements, and/or additionally or alternatively, a contribution to the specific fit with the patient-specific implant.

In particular embodiments, the customized surgical guides according to the invention are prepared by rapid manufacturing techniques, also referred to as layered manufacturing techniques or material deposition manufacturing techniques.

Rapid manufacturing includes all techniques whereby an object is built layer by layer or point per point by adding or hardening material (also called free-form manufacturing). The best known techniques of this type are stereolithography and related techniques, whereby for example a basin with liquid synthetic material is selectively cured layer by layer by means of a computer-controlled electromagnetic beam; selective laser sintering, whereby powder particles are sintered by means of an electromagnetic beam or are welded together according to a specific pattern; fused deposition modeling, whereby a synthetic material is fused and is stacked according to a line pattern; laminated object manufacturing, whereby layers of adhesive-coated paper, plastic, or metal laminates are successively glued together and cut to shape with a knife or laser cutter; or electron beam melting, whereby metal powder is melted layer per layer with an electron beam in a high vacuum.

In particular embodiments, Rapid Prototyping and Manufacturing (RP&M) techniques, are used for manufacturing the customized surgical guides of the invention. Rapid Prototyping and Manufacturing (RP&M) can be defined as a group of techniques used to quickly fabricate a physical model of an object typically using three-dimensional (3-D) computer aided design (CAD) data of the object. Currently, a multitude of Rapid Prototyping techniques is available, including stereo lithography (SLA), Selective Laser Sintering (SLS), Fused Deposition Modeling (FDM), foil-based techniques, etc.

A common feature of these techniques is that objects are typically built layer by layer. Stereo lithography, presently the most common RP&M technique, utilizes a vat of liquid photopolymer "resin" to build an object a layer at a time. On each layer, an electromagnetic ray, e.g. one or several laser beams which are computer-controlled, traces a specific pattern on the surface of the liquid resin that is defined by the two-dimensional cross-sections of the object to be formed. Exposure to the electromagnetic ray cures, or, solidifies the pattern traced on the resin and adheres it to the layer below. After a coat had been polymerized, the platform descends by a single layer thickness and a subsequent layer pattern is traced, adhering to the previous layer. A complete 3-D object is formed by this process.

Selective laser sintering (SLS) uses a high power laser or another focused heat source to sinter or weld small particles of plastic, metal, or ceramic powders into a mass representing the 3-dimensional object to be formed.

Fused deposition modeling (FDM) and related techniques make use of a temporary transition from a solid material to a liquid state, usually due to heating. The material is driven through an extrusion nozzle in a controlled way and deposited in the required place as described among others in U.S. Pat. No. 5,141,680.

Foil-based techniques fix coats to one another by means of gluing or photo polymerization or other techniques and cut the object from these coats or polymerize the object. Such a technique is described in U.S. Pat. No. 5,192,539.

Typically RP&M techniques start from a digital representation of the 3-D object to be formed. Generally, the digital representation is sliced into a series of cross-sectional layers which can be overlaid to form the object as a whole. The RP&M apparatus uses this data for building the object on a layer-by-layer basis. The cross-sectional data representing the layer data of the 3-D object may be generated using a computer system and computer aided design and manufacturing (CAD/CAM) software.

A selective laser sintering (SLS) apparatus is in particular embodiments used for the manufacture of the customized surgical tool from a computer model. It should be understood however, that various types of rapid manufacturing and tooling may be used for accurately fabricating these customized surgical guides including, but not limited to, stereolithography (SLA), Fused Deposition Modeling (FDM) or milling. Also, while rapid prototypic methods are particularly useful in the context of the present inventions, the guides according to the present invention can similarly be manufactured using other methods.

The surgical guides of the invention may be manufactured in different materials. Typically, only materials that are biocompatible (e.g. USP class VI compatible) with the human body are taken into account. Preferably the customized surgical guide is formed from a heat-tolerable material allowing it to tolerate high-temperature sterilization. In the case SLS is used as a RP&M technique, the surgical template may be fabricated from a polyamide such as PA 2200 as supplied by EOS, Munich, Germany or any other material known by those skilled in the art may also be used.

The invention further provides computer programs for performing the manufacturing methods of the present invention. More particularly, the present invention provides computer program products for enabling a device to execute at least part of the methods according to the invention described herein.

In particular embodiments, computer programs are provided for providing a design of a customized surgical guide comprising one or more custom guiding elements and/or one or more customized surface structures based on (1) one or more images of the bone and the patient-specific bone implant thereon; and (2) one or more screw trajectories determined by pre-operative planning, respectively. In particular embodiments, the one or more guiding elements of the guide are positioned corresponding to the pre-operatively planned screw insertions. Additionally or alternatively, the one or more customized surface structures of the guide are designed to ensure a unique fit between the patient-specific bone implant and the guide by way of a congruency or complementarity between the customized surface structure(s) and the patient-specific morphology of the patient-specific bone implant.

In further particular embodiments the computer programs further ensure the production of the surgical guide according to the invention by an additive manufacturing device. Suitable devices for manufacturing the guides according to the present invention are known to the skilled person and detailed hereinabove.

Yet a further aspect of the invention relates to the use of the customized surgical guides described herein to ensure stable fixation of a patient-specific implant. According to this aspect, the present invention provides methods for fixing a patient-specific bone implant onto a bone, which in particular embodiments comprises the steps of:

(a) placing a customized surgical guide according to the invention onto a patient-specific bone implant provided in the body;
(b) introducing the screw trajectories with the appropriate surgical tools;
(c) removing said customized surgical guide; and (optionally)
(d) fixing the patient-specific bone implant with screws onto the bone.

In particular embodiments, e.g. where self-tapering screws are used, the screw trajectories are established upon introduction of the screws in step (b). This may ensure the fixing of the implant onto the bone, such that step (d) is no longer or only partially required. In further particular embodiments, combinations of fastening tools are used More particularly, the step of placing a customized surgical guide according to the invention onto a patient-specific bone implant implies that the customized surgical guide is placed onto the patient-specific bone or joint implant such that it fits, mates, coincides and/or engages with the (specific) features of the patient-specific implant.

The methods according to this aspect of the invention further comprise the step of introducing the different screw trajectories with the appropriate surgical tools. As described above this includes but is not limited to a pre-drill, drill, a saw, jig saw, mill or lateral drill and fastening tools such as screw. Based on the position of the guides (and optionally the stops provided therein) an appropriate screw trajectory is provided.

The methods for fixing the patient-specific bone implant onto a bone according to the invention further comprise the step of removing the customized surgical guide. This step can be performed either before or after the implant has been fixed to the bone. According to particular embodiments, after the screw trajectories have been introduced, the surgical guide is removed in order to allow final fixation of the patient-specific implant onto the bone or joint. Alternatively, the implant is fixed to the bone first and the guide is removed thereafter. The methods of the present invention have the advantage that the patient-specific implant is already in place within the sometimes very narrow and deep surgical window, is maintained during introduction of the screw trajectories, and does not need to be removed prior to fixation.

Accordingly, the methods for fixing the patient-specific bone implant onto a bone further comprise, either before or after removal of the customized surgical guide, the step of (partly) fixing the patient-specific bone implant with screws onto the bone or joint. Tools for performing fixation with screws are known to the person skilled in the art.

The invention is further illustrated herein below by means of the following non-limiting embodiments.

In particular embodiments, the invention is applied for acetabular cup replacement and the custom surgical guides according to the present invention are designed to fit on a patient-specific acetabular implant. According to these embodiments, the connecting structure may be a ring structure and the at least one or more surface structures are designed to fit onto one or more surfaces of the patient-specific acetabular implant. For instance, in these embodiments, the one or more surfaces of the patient-specific acetabular implant may be designed based on specific anatomic features of one or more of the ilium, ischium and/or pubis of the hip joint.

Figure 3:
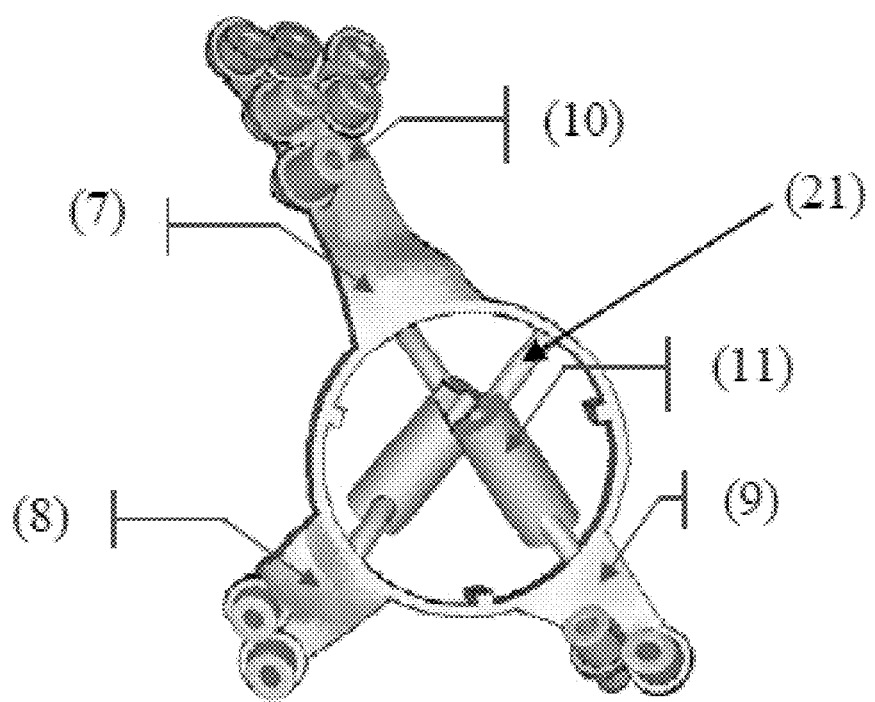
FIG. 3 A customized surgical guide according to a particular embodiment of the invention designed to fit on a patient-specific acetabular implant.

In particular embodiments, the present invention provides customized surgical guides for a patient-specific acetabular implant comprising one or more surface structures, and one or more guiding elements, wherein at least one of said one or more surface structures is designed to fit on the patient-specific acetabular implant. The acetabulum is the cup-shaped joint socket of the hip wherein the femur head articulates. In general, a joint prosthesis consists of a convex component that articulates in a concave socket, such as for instance in hip joint arthroplasty, a femoral head is mounted on a stem articulating in an acetabular cup. The following paragraph further describes the invention by means of the specific embodiment of a customized surgical guide for a patient-specific acetabular implant as illustrated in FIGS. 1 to 3.

The patient-specific acetabular implant according to the embodiment described herein comprises a hemispherical cup, which is rigidly connected to the host bone with projected patient-specific surfaces that provide intimate contact between the implant and the ilial, ischial and pubic host bones. FIG. 2A represents a severe acetabular defect of the left hemi-pelvis (1), which is to be treated with a patient-specific acetabular implant (2). A customized guide (3) according to the present invention as represented in FIGS. 1, 2C, 2D and 2E and 3 is designed that fits on the implant (2) to guide the planned drill directions (4) for the screws which will be inserted in a planned direction through the implant screw holes (12). The customized surgical guide (3) for a patient-specific acetabular implant consists of a central ring structure (5) mating with the acetabular rim (13) of the acetabular implant (2) as shown in FIGS. 2B, 2C and 2D. The customized surgical guide for the acetabular implant according to the present embodiment comprises one or more surface structures (7), (8) and (9), which comprise at least one implant-specific area of the external morphology by which the correct placement of the guide on the patient-specific implant is ensured. As shown in FIGS. 1 and 3, the one or more of the surface structures (7), (8), and (9) extend from the central ring (5) and comprise the one or more implant-specific areas, which are fully complementary to patient-specific areas (17), (18) and (19) of the external morphology of the acetabular implant. The side of each of these three surface structures which faces the bone is specifically designed to fit on anatomical features of each of the ilium, ischium and pubis, respectively. As presented in FIG. 2B, the patient-specific areas of the external morphology (17), (18) and (19) of the acetabular implant (2) comprise one or more screw holes (12). The one or more locking features (6) on the central ring (5), as presented in FIGS. 1 and 2D, add translational stability by preventing slide-off of the customized guide (3) in the plane of the acetabular rim (13). These locking features (6) still allow application of the customized guide (3) onto the patient-specific implant (2). Rotational stability, either uni- or bi-directionally, results primarily from the unique curvature fit of the contact area between the one or more surface structures (7), (8), and (9) and the patient-specific implant (2). Rotational stability can be further improved by adding locking features positioned on the surface structures (7), (8), and (9) of the customized guide, which mate with corresponding locking features present in the patient-specific implant (2). FIGS. 1 and 3 show cylindrical drill guiding elements (10) that are positioned on the surface structures of the customized guide (3) according to this specific embodiment to guide the insertion of a screw pre-drill instrument at the location of the implant screw holes (12) present in the surface structures (7), (8), and (9). In this specific embodiment, the pre-drilled screw holes are meant/suitable for cortical screws. Furthermore, additional (cylindrical drill) guiding elements (11) (shown in FIG. 3) are positioned on or within the cavity formed by the acetabular portion (14) (shown in FIG. 2B) of the patient-specific implant (2), being attached by bridging structures (21) (shown in FIG. 3) to the central ring (5), to guide the insertion of a screw pre-drill instrument at the location of the implant screw holes present in the acetabular portion (14). In this specific embodiment, the pre-drilled screw holes are meant/suitable for trabecular screws. In some embodiments, a portion of the drill guiding elements (11) may be positioned below the level of the plane formed by the acetabular rim (13) of the patient-specific implant (2). In general, cylindrical drill guiding elements (10) and (11) can be mutually intersecting to provide guidance and allow drilling within the available working space. In the present example this is the case for the cylindrical drill guiding element (11) in the cavity formed by the acetabular portion (14) of the implant (2), in order to enable drilling from within the available surgical window.

The diameter of cylindrical drill guiding elements (10) and (11) is determined based on the diameter of the pre-drill instrument, while the height is determined to provide sufficient stability and/or guidance of the same instrument. The cylindrical drill guiding elements (10) and (11) can also be trimmed either straight, obliquely, or with a complexly shaped cut in order to fit the surgical window. To solve visual orientation problems in case of obliquely trimmed cylinders, a disc-shaped visual reference ring (20), as shown in FIG. 2E, can be added at the base of the drill guiding cylinders (10) and (11) to provide visual feedback to the surgeon. The plane normal of the disc (20) equals the planned drill direction (4). As an additional or alternative visual reference, a wing element (22) as for example shown in FIG. 5, can be provided in case of drill guiding elements with overlying soft tissue. The wing is for example attached to a drill guiding element (10) or (11), or at some other location of the customized guide (3). The wing element provides visual feedback to the surgeon, minimizing potential misinterpretation resulting from obscured anatomical reference points, or potentially confusing orientations of the surface structures (7), (8) and (9) of the customized guide (3).

In the present embodiment, a cylindrical drill guiding element can be halved lengthwise, as illustrated by the halved cylindrical drill guiding element (23) in FIG. 6, allowing (partial) insertion of a screw directly in the implant, and subsequent removal of the customized guide with the inserted screw left in place. Doing so reduces degrees of freedom of the patient-specific implant (2) and customized guide (3) during drilling, and assures that correspondence between pre-drills and screw holes is not lost. In the present embodiment, the cylindrical guiding elements (10) and (11) may comprise an extension (16), shown in FIG. 4, into the implant screw hole, while still allowing insertion of the pre-drill instrument. Doing so reduces the degrees of freedom of the customized guide (3) relatively to the patient-specific implant (2). This is an example of an additional locking feature between guide and implant.

The invention claimed is:

1. A combination of a bone implant and a surgical guide for placement on a bone of a patient comprising:
a bone implant having an external morphology at least a portion of which functionally replaces an original anatomical feature of at least a portion of the patient's bone, and
a surgical guide for surgical instruments for placement on said bone implant, the surgical guide comprising:
(i) one or more surface structures comprising one or more flanges extending over at least part of said external morphology of the bone implant, wherein said external morphology of said bone implant has a surface that is complementary with a surface of said one or more surface structures and wherein a contact area between the one or more surface structures of the surgical guide and the surface of the bone implant has a three-dimensional fit that prevents both uni- or bi-directional translation along a first axis and uni- or bi-directional rotation around a second axis, so as to allow a stable fit between said surgical guide and said bone implant,
(ii) one or more guiding elements, wherein said one or more guiding elements are selected from the group consisting of drill guiding elements and cutting guiding elements, and
(iii) a central connecting structure that interconnects said one or more surface structures and said one or more guiding elements.

2. The combination according to claim 1, wherein said surgical guide is built layer by layer based on a three-dimensional computer aided design of the guide.

3. The combination according to claim 1, wherein said central connecting structure comprises one or more locking features.

4. The combination according to claim 1, wherein said surgical guide further comprises an element serving as a visual reference during surgery.

5. The combination according to claim 1, wherein said one or more cutting or drill guiding elements further comprise a cutting or drill stop.

6. The combination according to claim 1, wherein said bone implant is an acetabular implant having an acetabular rim, and wherein
said connecting structure is a ring structure, fitting on the acetabular rim of said acetabular implant; and
said surgical guide and said acetabular implant engage in said fit ensured by congruency between said external morphology of said acetabular implant and at least one of said one or more surface structures.

7. The combination according to claim 1 wherein said guide comprises two guiding elements having axes that are mutually intersecting.

8. The combination according to claim 1, wherein said surface structures comprise two or more flanges that extend along the surface of the implant.

9. A method for fixing a bone implant onto a bone, comprising the steps of:
(a) placing a surgical guide onto a bone implant, wherein the combination of said bone implant and said surgical guide is according to claim 1;
(b) drilling one or more screw hole trajectories;
(c) removing said surgical guide; and
(d) fixing said bone implant onto the bone with one or more screws.

10. A method for producing a surgical guide for surgical instruments for placement on a bone implant according to the combination of said bone implant and said surgical guide of claim 1, comprising:
(a) designing a surgical guide comprising one or more guiding elements and one or more surface structures based on:
an image of the bone and the bone implant thereon; and
one or more screw insertions corresponding to planned screw trajectories; and
(b) producing said surgical guide based on the design obtained in step (a), wherein:
(i) one or more of said one or more surface structures extend over at least part of the external morphology of the implant, and
(ii) one or more guiding elements are positioned corresponding to planned screw insertions, and
wherein said surgical guide and said bone implant engage by means of a fit ensured by congruency between said external morphology of said bone implant and at least one of said one or more surface structures.

11. The method according to claim 10, wherein said bone implant is an acetabular implant having an acetabular rim, and wherein
said connecting structure is a ring structure, fitting on the acetabular rim of said acetabular implant; and
said surgical guide and said acetabular implant engage in a fit ensured by congruency between said external morphology of said acetabular implant and at least one of said one or more surface structures.

12. The method according to claim 10, wherein said step of determining one or more screw trajectories using a planning comprises taking into account one or more of the following criteria:

obtaining a number of non-intersecting drill directions for screw trajectories;

ensuring screw trajectory length; and ensuring that the surrounding healthy soft tissue is preserved.

13. The method according to claim 10, wherein said surgical guide is produced layer by layer based on a three-dimensional computer aided design of the guide.

14. The combination according to claim 1, wherein at least one of the one or more flanges comprises one or more of the one or more guiding elements.

15. A combination of a bone implant and a surgical guide for placement on a bone of a patient comprising:

a bone implant having an external morphology at least a portion of which functionally replaces an original anatomical feature of at least a portion of the patient's bone, and a surgical guide for surgical instruments for placement on said bone implant, the surgical guide comprising:

(i) one or more surface structures comprising one or more flanges extending over at least part of said external morphology of the bone implant, wherein said external morphology of said bone implant has a surface that is complementary with a surface of said one or more surface structures to allow a stable fit between said surgical guide and said bone implant, (ii) one or more guiding elements, wherein said one or more guiding elements are selected from the group consisting of drill guiding elements and cutting guiding elements, and wherein the implant is provided with one or more holes, each of which is aligned with one of the one or more guiding elements, and (iii) a central connecting structure that interconnects said one or more surface structures and said one or more guiding elements.

\* \* \* \* \*